United States Patent
Baumeister

(10) Patent No.: US 11,759,750 B2
(45) Date of Patent: Sep. 19, 2023

(54) HOLLOW FIBER MEMBRANE BUNDLE

(71) Applicant: GAMBRO LUNDIA AB, Lund (SE)

(72) Inventor: Franz Baumeister, Uhldingen (DE)

(73) Assignee: GAMBRO LUNDIA AB, Lund (SE)

( * ) Notice: Subject to any disclaimer, the term of this patent is extended or adjusted under 35 U.S.C. 154(b) by 0 days.

(21) Appl. No.: 17/582,438

(22) Filed: Jan. 24, 2022

(65) Prior Publication Data

US 2022/0143556 A1     May 12, 2022

Related U.S. Application Data

(62) Division of application No. 16/497,607, filed as application No. PCT/EP2018/057852 on Mar. 28, 2018, now Pat. No. 11,260,349.

(30) Foreign Application Priority Data

Mar. 29, 2017 (SE) .................. 17163554-3

(51) Int. Cl.
    *B01D 63/02*     (2006.01)
    *B01D 69/08*     (2006.01)
    *A61M 1/16*     (2006.01)

(52) U.S. Cl.
    CPC ......... *B01D 63/023* (2013.01); *A61M 1/1621* (2014.02); *B01D 69/08* (2013.01); *A61M 2205/0272* (2013.01); *A61M 2207/00* (2013.01); *B01D 2313/04* (2013.01); *B01D 2313/23* (2013.01)

(58) Field of Classification Search
CPC .... B01D 63/023; B01D 63/021; B01D 69/08; B01D 2313/04; B01D 2313/23; B01D 65/006; B01D 67/0097; A61M 1/1621; A61M 2205/0272; A61M 2207/00; A41F 10/002; B65D 2313/04; H01F 7/0263; H01F 7/0215
See application file for complete search history.

(56) References Cited

U.S. PATENT DOCUMENTS

| | | | |
|---|---|---|---|
| 4,276,687 A * | 7/1981 | Schnell | .................. B65H 54/56 |
| | | | 242/157 R |
| 5,802,814 A | 9/1998 | Sano | |
| 2008/0041748 A1 | 2/2008 | Wood | |
| 2009/0321348 A1 | 12/2009 | Hormann | |
| 2013/0061431 A1 | 3/2013 | Naftali et al. | |
| 2014/0230369 A1 | 8/2014 | Reuschenbach et al. | |
| 2017/0275056 A1 | 9/2017 | Boudouris et al. | |

OTHER PUBLICATIONS

PCT Search Report and Written Opinion prepared for PCT/EP2018/057852, completed Jun. 26, 2018.

\* cited by examiner

*Primary Examiner* — Pranav N Patel
(74) *Attorney, Agent, or Firm* — BARNES & THORNBURG LLP

(57) ABSTRACT

The present disclosure relates to bundles of hollow fiber membranes and a process for their production. The bundles are used for the manufacture of filtration and/or diffusion devices, e.g., capillary dialyzers.

Figure 1:
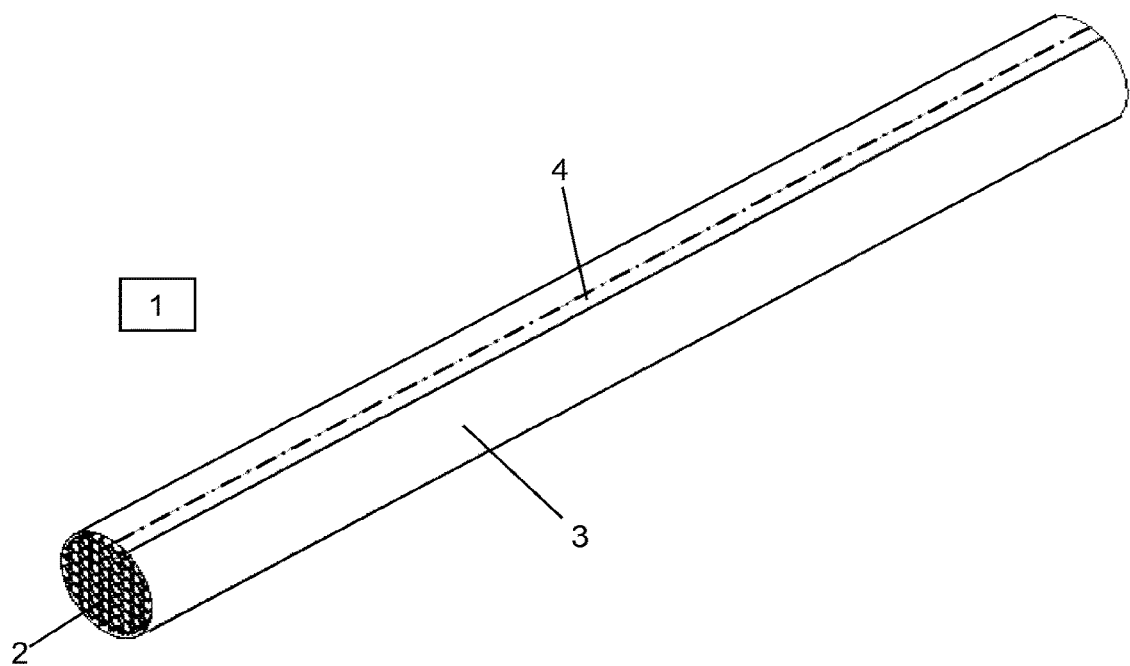

16 Claims, 2 Drawing Sheets ized by a magnetic closure.

HOLLOW FIBER MEMBRANE BUNDLE

CROSS-REFERENCE TO RELATED APPLICATIONS

This application is a divisional application of U.S. patent application Ser. No. 16/497,607, filed on Sep. 25, 2019, which is the U.S. national phase of PCT/EP2018/057852, filed on Mar. 28, 2018, which claims the benefit of European Patent Application Serial Number 17163554.3, filed on Mar. 29, 2017, the entire disclosures of all of which are incorporated herein by reference.

TECHNICAL FIELD

The present disclosure relates to bundles of hollow fiber membranes and a process for their production. The bundles are used for the manufacture of filtration and/or diffusion devices, e.g., capillary dialyzers.

DESCRIPTION OF THE RELATED ART

Several methods for producing hollow fiber membrane bundles wrapped with sheets of plastic film or paper have been described. The wrapping generally is sealed by welding or by use of an adhesive.

U.S. Pat. No. 4,276,687 A discloses a process for the production of hollow fiber bundles which involves winding the fibers onto a reel member to form an annular assembly of the fibers and thereafter cutting the annular assembly into separate bundles. Individual bundles are wrapped in a flexible paper sheet, e.g., a sheet of polypropylene paper, and cut at their ends.

WO 2016/102364 A1 discloses an apparatus for winding a foil around a strand of hollow fiber membranes having an irregular cross-section and forming the strand to circular bundles. The device comprises at least four form segments which can be moved towards the center of a circle individually. The contours of their profiles form a closed line of approximately circular shape when the segments are moved.

EP 2 420 464 B1 discloses an apparatus for wrapping a fiber bundle with a film. The apparatus comprises a receiver of first and second side elements and a flexible channel fastened between them for the reception of the film and the fiber bundle, and at least one folding device moveable transversely to the channel for the folding of the film around the fiber bundle. A drive is provided to move at least the first side element transversely to the channel, and a front edge of the first side element facing towards the channel can be moved past the front edge of the second side element facing towards the channel so that the flexible channel can be bent to form a cylinder.

GB 1 175 689 A discloses a method of making a dialyzer, comprising assembling a plurality of elongated laterally-aligned substantially parallel hollow filaments to form an elongated bundle, surrounding the elongated bundle with a flexible porous sleeve member, extending the sleeve member along the length of said bundle and causing a uniform reduction in the circumference of the sleeve member along the length of the bundle to constrain and laterally compress the bundle.

EP 0 639 383 B1 discloses a method of wrapping a bundle of fibers comprising the steps of applying a predetermined tension to the bundle longitudinally thereof and at opposite ends of the bundle; then wrapping a tape helically around the bundle and from one of the opposite ends towards the other end so that the tape covers the bundle almost entirely, while maintaining the tension applied thereto; and finally unwinding the tape off the bundle so as to expose the bundle gradually from the other end towards the one end, while inserting the thus exposed portion of the bundle gradually into a cylindrical protector.

DE 198 06 293 A1 discloses a method for wrapping a bundle of hollow fibers with a sheet of paper or plastic, which comprises positioning the sheet on a flexible support and depositing the bundle on top of the sheet, wrapping the side parts of the support including the sheet around the fiber bundle in such a manner that the sheet envelops the fiber bundle and its sides overlap to produce a cylindrical wrap.

When the fiber bundle is transferred into the housing of a filtration and/or diffusion device, the wrapping is removed and discarded, thus generating waste. It would be desirable to avoid the generation of waste wrapping material. It now has been found that waste generation can be avoided by sheeting the fiber bundles with a re-usable packaging material which is sealed magnetically.

SUMMARY

The present disclosure provides bundles of hollow fiber membranes enveloped in a magnetically sealed plastic film, i.e., a plastic film sealed by a magnetic closure, and a process for their production. The present disclosure also provides use of the fiber bundles in a process for the manufacture of filtration and/or diffusion devices.

SHORT DESCRIPTION OF THE DRAWINGS

Figure 2:
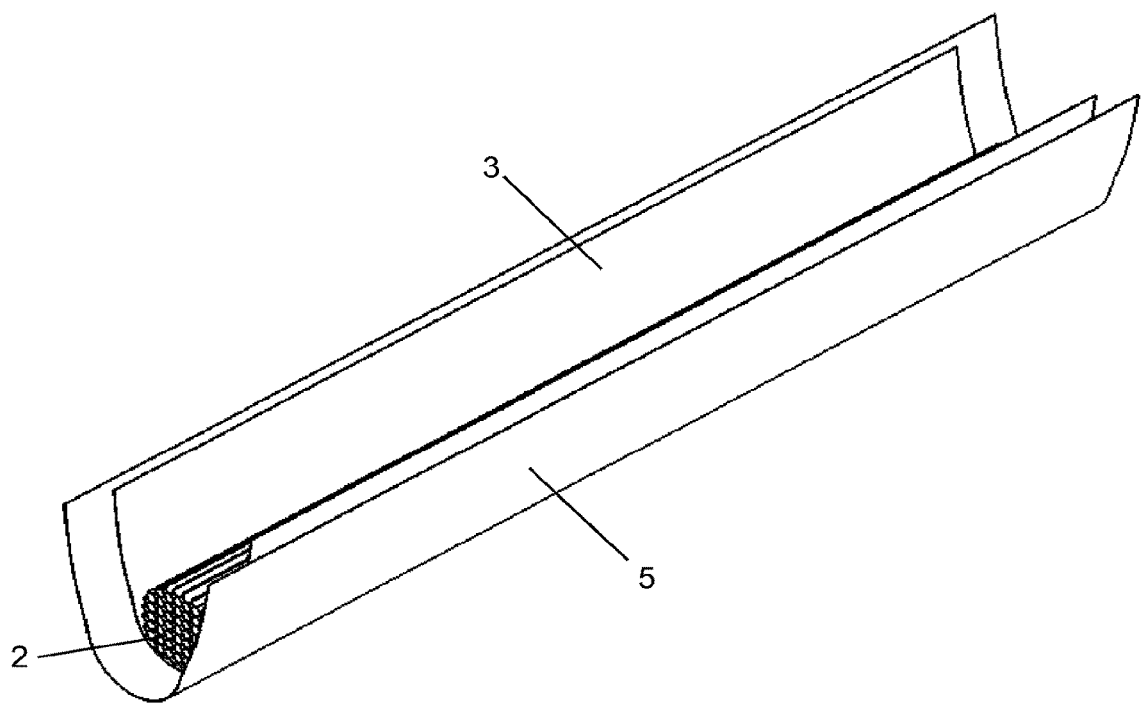
Figure 3:
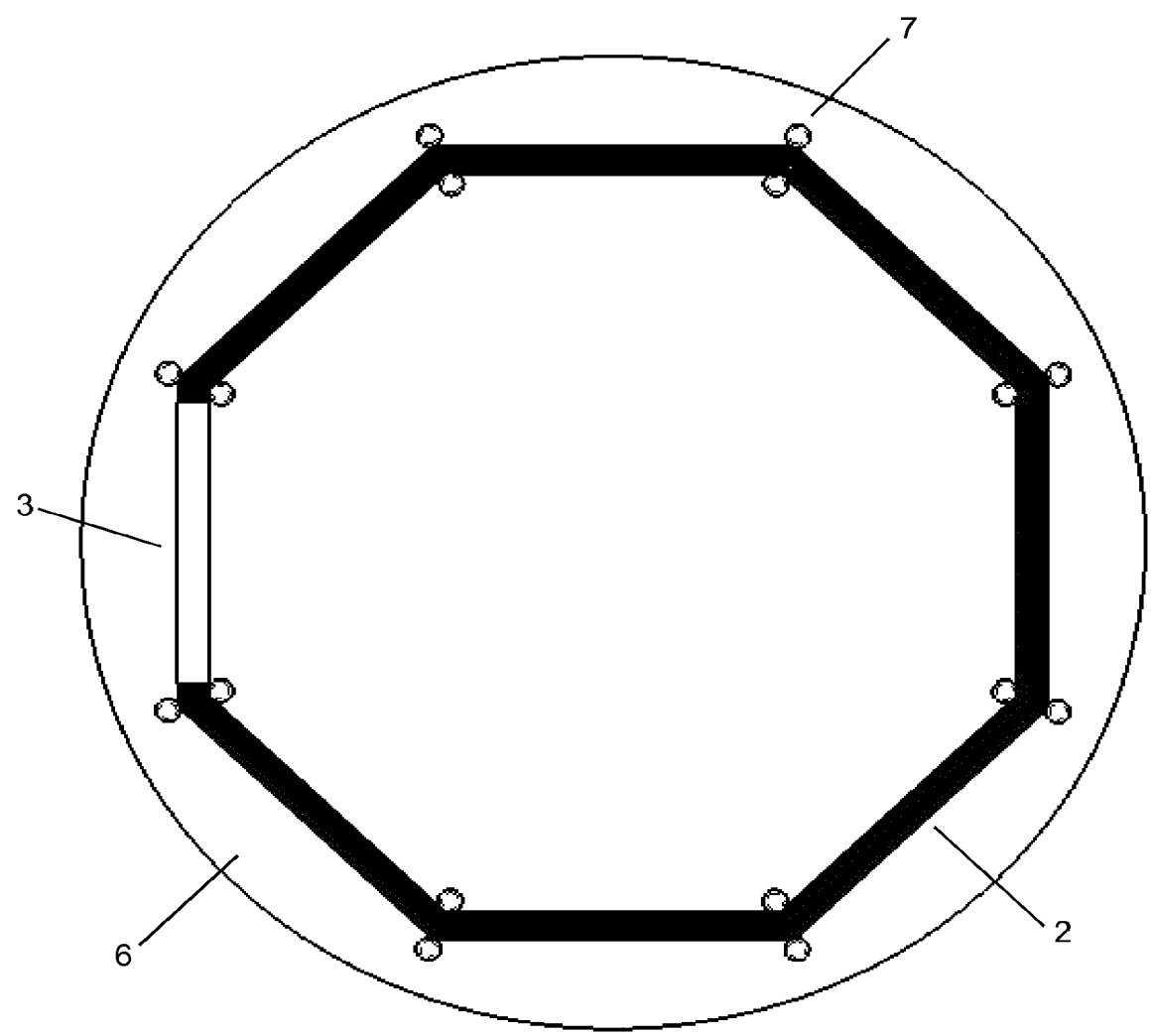

FIG. 1 is a schematic perspective view of a bundle 1 of hollow fiber membranes enveloped in a plastic film 3 sealed by a magnetic closure 4;

FIG. 2 shows a plurality of hollow fiber membranes 2 placed on a sheet of plastic film 3 comprising means for forming a magnetic closure, the plastic film 3 being positioned on a flexible support 5;

FIG. 3 shows a winding reel 6 with a strand of hollow fiber membranes 2. A part of the strand is enveloped with a plastic film 3 sealed by a magnetic closure.

DETAILED DESCRIPTION

The present disclosure provides a bundle of hollow fiber membranes enveloped in a magnetically sealed plastic film, i.e., a plastic film sealed by a magnetic closure.

A bundle of hollow fiber membranes suitable to be enveloped in a magnetically sealed plastic film, i.e., a plastic film sealed by a magnetic closure, can be produced by methods known to the person skilled in the art.

Exemplary methods include winding hollow fiber membranes onto a reel member to form an annular assembly of fibers and thereafter cutting the annular assembly into separate bundles; assembling a strand of hollow fiber membranes and forming the strand into a bundle of circular cross-section; or assembling a plurality of elongated laterally-aligned substantially parallel hollow fiber membranes to form an elongated bundle.

The plastic film used in the present disclosure comprises thermoplastic or thermosetting polymers. In one embodiment, the plastic film comprises at least one thermoplastic polymer. In one embodiment, the plastic film comprises a polyolefin. In a particular embodiment, the polyolefin is polyethylene.

The plastic film is magnetically sealable, i.e., capable of forming a magnetic closure. A sheet of the plastic film can be formed into a cylindrical shape, so that opposite edges of the sheet contact or overlap each other. The respective edges of the sheet adhere to each other by virtue of magnetic force, creating a magnetic seal (magnetic closure). To this end, the magnetically sealable sheet of plastic film features magnetic zones.

In one embodiment, the magnetic zones are located along the edges of the sheet which contact or overlap each other. In one embodiment, the magnetic zones are formed by strips of magnetic material on the surface or embedded in the bulk of the sheet. In another embodiment, the magnetic zones are formed by a magnetic coating on the surface of the sheet. In still another embodiment, the magnetic zones are formed by magnetic particles embedded in the bulk material of the respective zones of the sheet.

In a particular embodiment, the magnetic zones extend over the whole surface of the magnetically sealable sheet of plastic film. In one embodiment, a magnetic material is evenly distributed throughout the sheet.

In one embodiment, the magnetic material forming the magnetic zones of the magnetically sealable sheet of plastic film is a ferrimagnetic material. In one embodiment, the ferrimagnetic material comprises a ferrite. In one embodiment, the ferrite is a hard ferrite, for instance, a strontium ferrite, a barium ferrite, or a cobalt ferrite. In one embodiment, the hard ferrite is $SrO*6Fe_2O_3$. In another embodiment, the hard ferrite is $BaO*6Fe_2O_3$. In still another embodiment, the hard ferrite is $CoO*Fe_2O_3$.

In one embodiment, the magnetically sealable sheet of plastic film is comprised of a compound produced from hard ferrite powder and a thermoplastic polymer. The compound is extruded or calendered to form a film. During the process, the platelets of hard ferrite in the powder are mechanically oriented to enhance the magnetic properties of the film.

In a particular embodiment, the magnetically sealable plastic film comprises from 10 to 20 wt. % of a polyolefin and from 80 to 90 wt. % of a hard ferrite. An exemplary embodiment of the magnetically sealable plastic film comprises from 5 to 15 wt. % of polyethylene and from 85 to 95 wt. % of strontium ferrite, for instance, from 7 to 12 wt. % of polyethylene and from 88 to 93 wt. % of strontium ferrite. Optionally, the film comprises additives in an amount of up to 3 wt. %.

In one embodiment, the magnetically sealable plastic film has a thickness in the range of from 0.5 to 1.5 mm, e.g., 0.7 to 1.2 mm. The thickness of the film is important both for its flexibility and the strength of the magnetic seal that can be formed. A thinner film is more flexible, but generates less magnetic force. A thicker film generates more magnetic force, but cannot be shaped into cylinders having small diameter. In one embodiment, the minimum diameter of a cylinder that the film can be plied into is in the range of from 2 to 5 cm. In one embodiment, the magnetically sealable plastic film generates an adhesive magnetic force per area in the range of from 0.5 to 1.0 $N/cm^2$, for instance, from 0.6 to 0.8 $N/cm^2$.

The present disclosure also provides a process for producing a bundle of hollow fiber membranes enveloped in a magnetically sealed plastic film, i.e., a plastic film sealed by a magnetic closure. The process comprises wrapping a bundle of laterally aligned hollow fiber membranes with a magnetically sealable sheet of plastic film, i.e., a sheet of plastic film comprising means for forming a magnetic closure. In one embodiment, the individual fibers in the bundle are essentially parallel to each other. In another embodiment, only the ends of the individual fibers in the bundle are parallel, while the individual fibers have a helical conformation within the bundle.

Subsequent to wrapping the bundle with the sheet of plastic film comprising means for forming a magnetic closure, a magnetic seal is formed along the longitudinal seam of the sheet to produce a bundle of hollow fiber membranes enveloped in a magnetically sealed plastic film, i.e., a plastic film sealed by a magnetic closure.

In one embodiment, the means for forming a magnetic closure comprise at least one ferrimagnetic material. In one embodiment, the ferrimagnetic material is a hard ferrite.

In one embodiment, the magnetic seal is formed by contacting or overlapping opposite edges of a sheet of plastic film comprising a ferrimagnetic material. In one embodiment, the magnetically sealable sheet of plastic film features ferrimagnetic zones along the edges of the sheet. In another embodiment, the ferrimagnetic material is evenly distributed throughout the magnetically sealable sheet of plastic film.

In one embodiment, the process involves positioning the sheet of plastic film comprising means for forming a magnetic closure on a flexible support and depositing the bundle on top of the sheet, wrapping the side parts of the support including the sheet around the fiber bundle in such a manner that the sheet envelops the fiber bundle and its edges contact or overlap to produce a cylindrical wrap. FIG. 2 shows a plurality of hollow fiber membranes 2 placed on a magnetically sealable sheet of plastic film 3 positioned on a flexible support 5.

In another embodiment, the process involves providing a strand of hollow fiber membranes on a winding reel, wrapping sections of the strand with the sheet of plastic film comprising means for forming a magnetic closure in such a manner that the sheet envelops the fiber bundle and its edges contact or overlap to produce a cylindrical wrap, and cutting a wrapped bundle from the strand. FIG. 3 shows a winding reel 6 with a strand of hollow fiber membranes 2. The strand is held by fork members 7. A section of the strand is enveloped with a plastic film 3 sealed by a magnetic closure. To produce a bundle 1, the strand is cut on both sides of the plastic film 3.

In one embodiment, the edges of the sheet of plastic film comprising means for forming a magnetic closure overlap after wrapping the bundle of hollow fiber membranes; and the overlapping zone has a width of 1 to 5 cm, for instance, 1 to 2 cm. FIG. 1 shows a schematic perspective view of such a bundle 1 of hollow fiber membranes 2 enveloped in a plastic film 3 sealed by a magnetic closure 4. The overlapping zone forms the magnetic closure 4.

The present disclosure also provides a process for the production of a filtration and/or diffusion device which uses a bundle of hollow fiber membranes enveloped in a plastic film sealed by a magnetic closure. The process comprises transfer of the enveloped bundle into a housing, e.g. a tubular filter casing, and the removal of the plastic film from the bundle.

In one embodiment of the process, the enveloped bundle is introduced into the housing; one end of the bundle of hollow fiber membranes is pushed in longitudinal direction, so that its other end protrudes from the plastic film sealed by a magnetic closure; and the plastic film sealed by a magnetic closure is pulled from the housing in the opposite direction.

In one embodiment, the process further comprises opening the magnetic closure of the plastic film and reusing the sheet of plastic film in the production of another bundle of hollow fiber membranes enveloped in a plastic film sealed by a magnetic closure.

Once the magnetic closure of the plastic film has been opened, the sheet of plastic film returns to its initial form and can be used to wrap another bundle of hollow fiber membranes. It is an advantage of the process that the sheet of plastic film comprising means for forming a magnetic closure can be reused in the production of further bundles of hollow fiber membranes and further filtration and/or diffusion devices, thus avoiding waste.

The invention claimed is:

1. A process for the production of a filtration and/or diffusion device, comprising transfer of a bundle of hollow fiber membranes enveloped in a plastic film sealed by a magnetic closure into a housing; and removal of the plastic film from the bundle,
wherein the magnetic closure comprises a plurality of magnetic particles, and
wherein the plurality of magnetic particles are distributed throughout the plastic film.

2. A process for the production of a filtration and/or diffusion device, comprising transfer of a bundle of hollow fiber membranes enveloped in a plastic film sealed by a magnetic closure into a housing; and removal of the plastic film from the bundle, and further comprising opening the magnetic closure of the plastic film and reusing the sheet of plastic film in the production of another bundle of hollow fiber membranes enveloped in a plastic film sealed by a magnetic closure,
wherein the magnetic closure comprises a plurality of magnetic particles, and
wherein the plurality of magnetic particles are distributed throughout the plastic film.

3. The process of claim 1, wherein the magnetic closure is embedded in the plastic film.

4. The process of claim 1, wherein the plastic film comprises a polyolefin.

5. The process of claim 1, wherein the magnetic particles comprise a ferrimagnetic material.

6. The process of claim 5, wherein the ferrimagnetic material comprises a hard ferrite.

7. The process of claim 6, wherein the hard ferrite is selected from the group consisting of a strontium ferrite, a barium ferrite, a cobalt ferrite, $SrO*6Fe_2O_3$, or any combination thereof.

8. The process of claim 1, wherein the magnetic closure is formed by overlapping edges of the plastic film.

9. The process of claim 1, wherein the plurality of magnetic particles are evenly distributed throughout the plastic film.

10. The process of claim 2, wherein the magnetic closure is embedded in the plastic film.

11. The process of claim 2, wherein the plastic film comprises a polyolefin.

12. The process of claim 2, wherein the magnetic particles comprise a ferrimagnetic material.

13. The process of claim 12, wherein the ferrimagnetic material comprises a hard ferrite.

14. The process of claim 13, wherein the hard ferrite is selected from the group consisting of a strontium ferrite, a barium ferrite, a cobalt ferrite, $SrO*6Fe_2O_3$, or any combination thereof.

15. The process of claim 2, wherein the magnetic closure is formed by overlapping edges of the plastic film.

16. The process of claim 2, wherein the plurality of magnetic particles are evenly distributed throughout the plastic film.

* * * * *